United States Patent
Rao et al.

(10) Patent No.: US 10,301,282 B2
(45) Date of Patent: May 28, 2019

(54) POLYMORPHIC FORM X OF NILOTINIB DIHYDROCHLORIDE HYDRATE

(71) Applicant: Cipla Limited, Mumbai (IN)

(72) Inventors: Dharmaraj Ramachandra Rao, Mumbai (IN); Geena Malhotra, Mumbai (IN); Srinivas Laxminarayan Pathi, Bangalore (IN); Venugopalarao Chinimilli, Bangalore (IN); Manish Gopaldas Gangrade, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/559,325

(22) PCT Filed: Mar. 21, 2016

(86) PCT No.: PCT/GB2016/050775
§ 371 (c)(1),
(2) Date: Sep. 18, 2017

(87) PCT Pub. No.: WO2016/151304
PCT Pub. Date: Sep. 29, 2016

(65) Prior Publication Data
US 2018/0111915 A1    Apr. 26, 2018

(30) Foreign Application Priority Data
Mar. 20, 2015  (IN) .......................... 941/MUM/2015

(51) Int. Cl.
*C07D 401/14*    (2006.01)

(52) U.S. Cl.
CPC ........ *C07D 401/14* (2013.01); *C07B 2200/13* (2013.01)

(58) Field of Classification Search
CPC .................................................... C07D 401/14
See application file for complete search history.

(56) References Cited

U.S. PATENT DOCUMENTS

| 7,169,791 | B2 | 1/2007 | Breitenstein et al. |
| 8,163,904 | B2 | 4/2012 | Manley et al. |

FOREIGN PATENT DOCUMENTS

| IN | 941/MUM/2015 | 3/2015 |
| WO | 2011033307 A1 | 3/2011 |
| WO | 2016151304 A1 | 9/2016 |

OTHER PUBLICATIONS

Kakkar et al. Drug Development and Industrial Pharmacy, 23(11), pp. 1063-1067 . (Year: 1997).*
Foreign communication from a related application—International Search Report and Written Opinion of International Application No. PCT/GB2016/050775, dated Jun. 3, 2016, 11 pages.
Foreign communication from a related application—International Preliminary Report on Patentability of International Application No. PCT/GB2016/050775, dated Sep. 26, 2017, 9 pages.
Byrn, Stephen, et al., "Pharmaceutical Solids: A Strategic Approach to Regulatory Considerations," Pharmaceutical Research, 1995, pp. 945-954, vol. 12, No. 7, Plenum Publishing Corporation.
Foreign communication from a related application—Official Action issued in European Application No. 16 713 566.4, dated Aug. 23, 2018, 5 pages.

* cited by examiner

*Primary Examiner* — Emily A Bernhardt
(74) *Attorney, Agent, or Firm* — Conley Rose, P.C.; Rodney B. Carroll

(57) ABSTRACT

The present invention relates to a novel polymorph of nilotinib hydrochloride (Form X), to processes for its preparation, to pharmaceutical compositions containing the same and to its use in medicine.

15 Claims, 2 Drawing Sheets

POLYMORPHIC FORM X OF NILOTINIB DIHYDROCHLORIDE HYDRATE

CROSS REFERENCE TO RELATED APPLICATIONS

This application is a filing under 35 U.S.C. 371 of International Application No. PCT/GB2016/050775 filed Mar. 21, 2016, entitled "Novel Polymorphic Form X of Nilotinib Dihydrochloride Hydrate" which claims priority to Indian Patent Application No. 941/MUM/2015 filed Mar. 20, 2015, which applications are incorporated by reference herein in their entirety.

FIELD OF THE INVENTION

The present invention relates to a novel polymorph of nilotinib hydrochloride, to processes for its preparation, to pharmaceutical compositions containing it and to its use in medicine.

BACKGROUND OF THE INVENTION

Chronic myelogenous leukemia (CML) accounts for approximately 20% of all leukemia cases. The chromosomal translocation known as the Philadelphia chromosome is a specific genetic abnormality in leukemia cancer cells. In this translocation, a single multipotent hematopoietic stem cell undergoes genetic rearrangement between two chromosomes (the 9th and 22nd). As a result, part of the BCR ("breakpoint cluster region") gene from chromosome 22 is fused with the ABL (Abelson leukemia) gene on chromosome 9. This abnormal "fusion" gene generates a protein of p210 or sometimes p185 weight (p210 is short for 210 kDa protein, a shorthand used for characterizing proteins based solely on size). Because ABL carries a domain that can add phosphate groups to tyrosine residues (a tyrosine kinase), the BCR-ABL fusion gene product is also a tyrosine kinase.

BCR-ABL activates a cascade of proteins that control the cell cycle, speeding up cell division. Moreover, the BCR-ABL protein inhibits DNA repair, causing genomic instability and making the cell more susceptible to developing further genetic abnormalities. The action of the BCR-ABL protein is the pathophysiologic cause of chronic myelogenous leukemia.

With improved understanding of the nature of the BCR-ABL protein and its action as a tyrosine kinase, targeted therapies that specifically inhibit the activity of the BCR-ABL protein, have been developed, the first of which was imatinib mesylate. These tyrosine kinase inhibitors can induce complete remissions in CML, confirming the central importance of BCR-ABL as the cause of CML.

Nilotinib is a phenylaminopyrimidime derivative structurally related to imatinib that selectively inhibits the BCR-ABL tyrosine kinase.

Nilotinib is chemically termed as 4-methyl-N-[3-(4-methyl-1H-imidazol-1-yl)-5-(trifluoromethyl)phenyl]-3-[(4-pyridin-3-ylpyrimidin-2-yl)amino]benzamide and has the structural formula I:

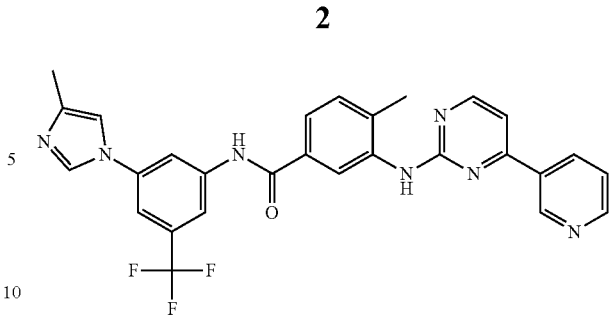

Nilotinib and its process of preparation are disclosed in U.S. Pat. No. 7,169,791 B2.

A particularly useful salt of nilotinib is nilotinib hydrochloride monohydrate as disclosed in U.S. Pat. No. 8,163,904 B2. This patent discloses two polymorphic forms of nilotinib hydrochloride monohydrate namely, "Form A" and "Form B". The patent also discloses various other salts of nilotinib, namely monophosphate, diphosphate, sulfate, mesylate, esylate, besylate and tosylate and processes for their preparation. Example 1 of U.S. Pat. No. 8,163,904 describes a process for preparing nilotinib hydrochloride monohydrate, the resulting product of which is characterized by an X-Ray diffraction (XRD) pattern having peaks at 7.4, 9.4, 11.6, 12.1, 15.8, 19.3, 22.1, 24.1 and 25.7±0.2°2θ. Form B is described in U.S. Pat. No. 8,163,904 as being hygroscopic and very slightly soluble in water.

WO2011/033307 discloses nilotinib dihydrochloride dihydrate characterized by XRD, Differential scanning calorimetry (DSC) and Thermogravimetric analysis (TGA). Also disclosed are processes of preparation and pharmaceutical compositions containing these compounds as well as the use of the compounds in the treatment of cancer. Nilotinib dihydrochloride dihydrate disclosed in WO2011/033307 is characterised by (i) an XRD pattern comprising peaks at 7.18, 14.32, 23.34 and 27.62±0.2°2θ; and (ii) a DSC thermogram with endothermic peaks at about 107±2° C. and 251±2° C.

One important property associated with solid state forms of drug substances is their aqueous solubility. Compounds having poor water solubility can lead to limited oral bioavailability when administered in patients. In such cases, the discovery of new polymorphic forms and solvates of a pharmaceutically useful compound with improved aqueous solubility provides a significant opportunity to increase the performance characteristics of the active pharmaceutical ingredient (API). The increase in performance may be seen in oral bioavailability, flowability and solubility thus reducing the dosage required for the patient.

There is a continued need to contribute towards enhancing the properties of nilotinib, particularly with respect to solubility and industrial feasibility.

OBJECT OF THE INVENTION

The object of the present invention is to provide a novel polymorph of nilotinib hydrochloride which is free from other polymorphs and/or solvates, and processes for its preparation.

SUMMARY OF THE INVENTION

In a first aspect, the present invention provides a novel polymorph of nilotinib hydrochloride.

Preferably, the nilotinib hydrochloride of the present invention is nilotinib dihydrochloride. The dihydrochloride salt of nilotinib according to the present invention may be in a pseudopolymorphic form. Pseudopolymorphs provided include hydrates and/or solvates. More preferably, the nilotinib hydrochloride of the present invention is nilotinib dihydrochloride hydrate. In one aspect of the present invention, there is provided a non-stoichiometric hydrate of nilotinib dihydrochloride.

A particularly preferred form of nilotinib dihydrochloride hydrate according to the present invention is designated herein as "Form X". Nilotinib dihydrochloride hydrate Form X of the present invention is crystalline in nature and characterized by a unique XRD pattern and IR spectrum.

The novel crystalline form of the present invention (Form X) possesses certain physical and chemical properties which render it particularly suitable for pharmaceutical development, such as good solubility, permeability and bioavailability. In addition, it is suitable for bulk handling and formulation.

In a further aspect of the present invention, there are provided processes for preparing a hydrate of nilotinib dihydrochloride, particularly nilotinib dihydrochloride hydrate Form X. The processes of the present invention afford nilotinib dihydrochloride hydrate in high purity and high yield. Advantageously, they are environment friendly and suitable for use on a commercial scale.

In a further aspect of the present invention, there is provided a pharmaceutical composition comprising nilotinib dihydrochloride hydrate Form X and optionally one or more pharmaceutically acceptable excipients.

In a further aspect of the present invention, there is provided a method for preparing a pharmaceutical composition comprising nilotinib dihydrochloride hydrate Form X, which method comprises admixing nilotinib dihydrochloride hydrate Form X with one or more pharmaceutically acceptable excipients.

In a further aspect of the present invention, there is provided method for the prevention or treatment of a disease which responds to a protein kinase activity which method comprises administering nilotinib dihydrochloride hydrate Form X to a patient in need thereof. The method of treatment is particularly suitable for treating adults with chronic phase and accelerated phase Philadelphia chromosome positive chronic myelogenous leukemia (CML) with resistance or intolerance to prior therapy, including imatinib.

In a further aspect of the present invention, there is provided nilotinib dihydrochloride hydrate Form X for use in the prevention or treatment of a disease which responds to a protein kinase activity, including Philadelphia chromosome positive chronic myelogenous leukemia (CML) in the chronic phase.

In a further aspect of the present invention, there is provided nilotinib dihydrochloride hydrate Form X for use in the manufacture of a medicament for the prevention or treatment of a disease which responds to a protein kinase activity, including Philadelphia chromosome positive chronic myelogenous leukemia (CML) in the chronic phase.

DETAILED DESCRIPTION OF THE INVENTION

Figure 1:
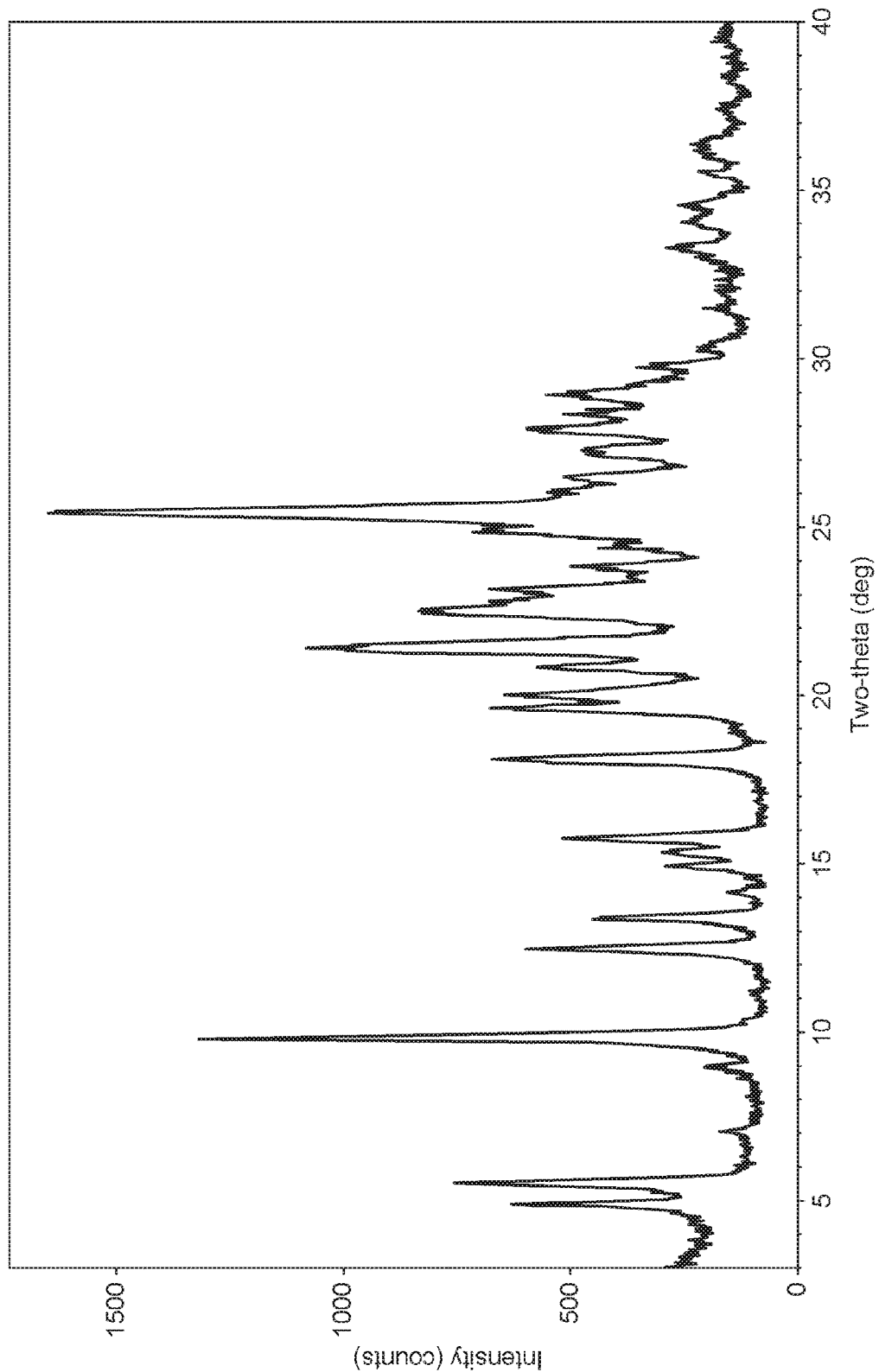
FIG. 1 is X-ray powder diffraction spectrum of crystalline nilotinib dihydrochloride hydrate Form X.

As used herein, the term "hydrate" refers to a substance that is formed by the addition of water to a substance pre-existing in the solid-state, e.g. nilotinib hydrochloride. The water molecules may be absorbed, adsorbed and/or contained within the crystal lattice of the solid compound and are usually present in a defined stoichiometric ratio. The notation for a hydrated compound (M) may be M.nH$_2$O, where n is the number of water molecules per formula unit of the compound. For example, in a hemihydrate, n is 0.5; in a monohydrate n is 1; in a sesquihydrate, n is 1.5; in a dihydrate, n is 2; and so on.

In comparison to the restricted stoichiometric hydrates, non-stoichiometric hydrates can vary in water content without a major change in their crystal structure. The amount of water in the crystal lattice only depends on the partial pressure of water in the surrounding atmosphere.

Structurally, non-stoichiometric hydrates normally show channels or networks, through which the water molecules can diffuse. Depending on how the water is arranged inside the crystals, they are classified as isolated hydrates, channel hydrates and ion associated hydrates.

As used herein, the term "substantially the same X-ray powder diffraction pattern" is understood to mean that those X-ray powder diffraction patterns having diffraction peaks with 2θ values within ±0.2. Thus, the diffraction pattern referred to herein is within the scope of the diffraction pattern of the present invention.

Acid addition salts of nilotinib may be isolated as either mono- or di-acid addition salts and/or solvates thereof having either 1 or 2 acid molecules per nilotinib molecule respectively. In one aspect, the present invention provides a hydrochloric acid addition salt of nilotinib. The hydrochloride salt may be isolated in pseudopolymorphic form, preferably in hydrated form.

The ratio of nilotinib to hydrochloric acid may range from about 1 to about 2 molecules of hydrochloric acid per 1 molecule of nilotinib. Preferably, the ratio is 2 molecules of hydrochloric acid per 1 molecule of nilotinib of formula I, i.e. nilotinib dihydrochloride.

As polymorphic forms may be reliably characterised by peak positions in the X-ray diffractogram, the polymorph of the present invention has been characterised by powder X-ray diffraction spectroscopy which produces a fingerprint of the particular crystalline form. Measurements of 2θ values are accurate to within ±0.2 degrees. The powder diffraction patterns employed to characterize the novel polymorph of the present invention were measured on a Rigaku Dmax 2200 advanced X-ray powder diffractometer with a copper-K-α radiation source, using conventional analytical methods known in the art.

The polymorph of the present invention has been further characterized by FT-IR spectroscopy. The IR spectra were measured on KBr disks using a Bruker Alpha FT-IR spectrometer at resolution 4 cm$^{-1}$. The characteristic absorption bands are expressed in cm$^{-1}$.

It will be appreciated that other conventional analytical methods including, but not limited to, intrinsic dissolution profiles, solid state NMR, Thermogravimetric analysis (TGA), Differential Scanning calorimetric analysis (DSC), Dynamic Vapour Sorption analysis (DVS) and Raman spectroscopy may also be employed to characterize the novel polymorph of the present invention.

Nilotinib dihydrochloride hydrate as referred to herein includes various hydrated forms, such as nilotinib dihydrochloride monohydrate and nilotinib dihydrochloride monohydrate. A particularly preferred hydrate of nilotinib dihydrochloride according to the present invention is nilotinib dihydrochloride hydrate Form X. Advantageously, nilotinib dihydrochloride hydrate Form X is substantially non-hygroscopic and has good flow characteristics.

In another aspect, the present invention provides a process for preparing nilotinib dihydrochloride hydrate Form X in high yield and purity. The present invention also provides pharmaceutical compositions comprising nilotinib dihydrochloride hydrate Form X.

The water content present in nilotinib dihydrochloride may vary depending upon the conditions under which it is prepared and stored. In the case of nilotinib dihydrochloride hydrate Form X, the amount of water present may range from about 4.0 wt % to about 6.0 wt % per molecule of nilotinib. While between about 4.0 wt % and about 6.0 wt % of water per molecule of nilotinib represent the lower and upper observed ranges respectively; the actual water content of the crystalline form may vary within this range depending on external factors such as the temperature of the crystalline form. Water content may be measured using conventional analytical techniques such as the Karl Fischer method.

Thus, it has been unexpectedly found that nilotinib dihydrochloride forms a stable, non-hygroscopic crystalline hydrate with water, wherein the molar ratio of nilotinib to hydrochloric acid is approximately 1:2 and wherein water is present in the non-stoichiometric ratio ranging from about 4.0 wt % to about 6.0 wt % per molecule of nilotinib.

The crystalline Form X of nilotinib dihydrochloride hydrate has an XRD pattern with a characteristic peak at 25.60±0.2°2θ. The XRD pattern has further characterising peaks at 5.617, 9.941, 19.700, 20.080, 21.520, 22.620, and 24.939±0.2°2θ. The XRD pattern may have still further characterising peaks at 4.977, 12.560, 15.801, 18.180, 20.899, 27.961, 28.419, and 28.999±0.2°2θ.

In one aspect of the invention, the crystalline Form X of nilotinib dihydrochloride hydrate has an XRPD pattern with those peaks at °2θ values±0.2°2θ as depicted in Table 1. In another aspect, the crystalline Form X of nilotinib dihydrochloride hydrate has substantially the same XRPD pattern with peaks at 2θ values as depicted in Table 1.

TABLE 1

| Peak value (°2θ) | Relative Intensity [%] |
| --- | --- |
| 4.977 | 30.0 |
| 5.617 | 36.8 |
| 9.941 | 53.5 |
| 12.560 | 22.7 |
| 15.801 | 23.2 |
| 18.180 | 29.6 |
| 19.700 | 41.9 |
| 20.080 | 34.9 |
| 20.899 | 15.4 |
| 21.520 | 56.3 |
| 22.620 | 55.9 |
| 24.939 | 58.7 |
| 25.600 | 100.0 |
| 27.961 | 15.2 |
| 28.419 | 16.9 |
| 28.999 | 15.2 |

Crystalline Form X of nilotinib dihydrochloride hydrate of the present invention may be characterized as having an X-ray powder diffraction spectrum as shown in FIG. 1.

Crystalline Form X of nilotinib dihydrochloride hydrate of the present invention may be characterized as having characteristic IR spectrum peaks at about 3425 $cm^{-1}$, 3235 $cm^{-1}$, 3122 $cm^{-1}$, 2933 $cm^{-1}$, 2776 $cm^{-1}$, 2625 $cm^{-1}$, 1670 $cm^{-1}$, 1619 $cm^{-1}$, 1543 $cm^{-1}$, 1506 $cm^{-1}$, 1492 $cm^{-1}$, and 1114 $cm^{-1}$.

Figure 2:
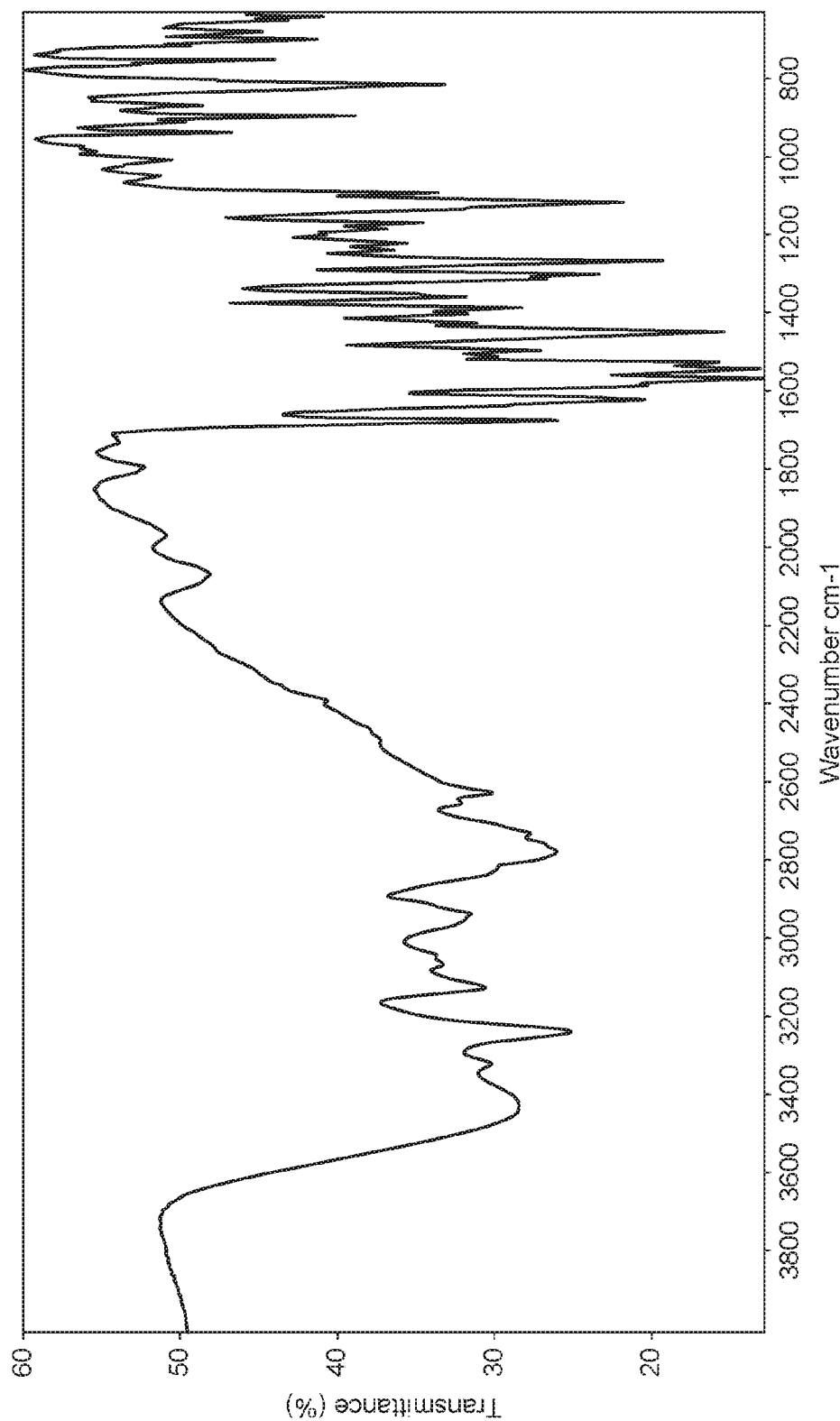
FIG. 2 is an Infra-Red (IR) spectrum of crystalline nilotinib dihydrochloride hydrate Form X.

The crystalline Form X of nilotinib dihydrochloride hydrate of the present invention may be characterized by having an IR spectrum as shown in FIG. 2.

Those skilled in the art will recognize that Form X may be further characterized by other methods including, but not limited to DSC, TGA, DVS, intrinsic dissolution, solid state NMR and Raman spectroscopy.

In still another aspect, the present invention provides a Form X of nilotinib dihydrochloride which is non-hygroscopic (or non-hydroscopic) and has good flow characteristics.

Intrinsic dissolution studies were conducted on nilotinib dihydrochloride Form X and nilotinib monohydrochloride monohydrate in 0.1 N HCl using a conventional intrinsic dissolution assembly. It was observed that the release of nilotinib dihydrochloride Form X of was 109% at 15 minutes time interval, whereas the release of nilotinib monohydrochloride monohydrate was 114% at 15 minutes time interval. These data indicate that intrinsic dissolution of nilotinib dihydrochloride Form X and nilotinib monohydrochloride monohydrate are comparable when measured under analogous conditions.

Nilotinib dihydrochloride Form X of the present invention preferably exhibits a bulk density in the range from about 0.140 to about 0.142 g/ml and a tapped density in the range from about 0.217 to about 0.129 g/ml when measured using conventional methods known in the art. In comparison, the nilotinib monohydrochloride monohydrate exhibits a bulk density in the range from about 0.123 to about 0.125 g/ml and a tapped density in the range from about 0.197 to about 0.199 g/ml when measured using the same methodology.

The bulk and tapped densities of nilotinib dihydrochloride Form X of the present invention are advantageous in the formulation of Form X into pharmaceutical dosage forms, especially tablet formulations. For example, Form X's higher density will give rise to a more compressible formulation (i.e. better compressibility). As such, Form X of the present invention is able to provide comparable dissolution characteristics but with the advantage of the Form X being more suitable for pharmaceutical formulation.

According to another aspect of the present invention there is provided a process for the preparation of the crystalline Form X of nilotinib dihydrochloride hydrate. The process may comprise:
(i) mixing nilotinib dihydrochloride in one or more non-polar solvents,
(ii) adding one more polar solvents, and
(iii) crystallizing Form X of nilotinib dihydrochloride hydrate from the resulting solution.

Alternatively, crystalline Form X of nilotinib dihydrochloride hydrate may prepared by a process comprising the steps of:
(i) mixing nilotinib dihydrochloride in a mixture of one more non-polar solvents and one or more polar solvents, and
(ii) crystallizing Form X of nilotinib dihydrochloride hydrate from the resulting solution The nilotinib dihydrochloride salt used in the preparation of the Form X may be any polymorphic form or any mixture of polymorphic forms wherein the said nilotinib dihydrochloride is hydrated, solvated, non-solvated or mixture of hydrated, solvated or non-solvated forms thereof. In a preferred embodiment, nilotinib dihydrochloride is provided in the form of nilotinib dihydrochloride dihydrate.

The nilotinib dihydrochloride, used for the above process, as well as for the following processes described in this application can be obtained by any known method.

In an embodiment the term "mixing" is understood as suspending or dissolving nilotinib dihydrochloride in a solvent or solvent mixture, wherein a solvent is selected from nonpolar solvent and polar solvent.

In one aspect of the present invention, the nonpolar solvent is selected from, but not limited to, hexane, heptane, toluene, xylene and chlorinated solvents such as dichloromethane, chloroform, carbon tetrachloride or any combination mixture thereof.

In another aspect of the present invention, the polar solvent is selected from, but not limited to, the group comprising of C1-C4 alcohols, ketones, esters, acetonitrile or any combination thereof preferably, C1-C4 alcohol is selected from methanol, ethanol, isopropanol, n-propanol, isobutanol, n-butanol and t-butanol. Most preferably C1-C4 alcohol is selected from methanol, ethanol and isopropanol.

A particularly preferred combination of solvents is methanol and toluene.

The ratio of nonpolar solvent to polar solvent may vary from about 1:1 to about 1:2. Most preferably the ratio is 1:1.

Mixing may take place at a temperature ranging from about ambient temperature to about 110° C., preferably the reflux temperature at atmospheric pressure of the solvent or of the solvent mixture selected.

Addition of the polar solvent may take place at the reflux temperature at atmospheric pressure of the solvent or of the solvent mixture selected.

Form X may be crystallized from the solvent solution by conventional methods including cooling, chilling, stirring, seeding and evaporation of the portion of the solvent. A preferred method comprises cooling the solution slowly to ambient temperature and stirring the solution for a prolonged period of time, suitably for at least 10 hours. Optionally, the solution may be further cooled to a temperature in the range from about 0 to about 5° C. and maintained for about 30 to 60 minutes. The crystals thus formed are preferably isolated by filtration using conventional means.

The crystalline Form X of nilotinib dihydrochloride hydrate obtained according to the present invention is substantially free from other forms of nilotinib. "Substantially free from other forms of nilotinib" shall be understood to mean containing less than 10%, preferably less than 5%, of any other crystalline forms of nilotinib and less than 1% of other impurities or solvates.

The process of invention may be used as a method for purifying any form of nilotinib, as well as for the preparation of Form X.

According to yet another aspect of the present invention there is provided use of the crystalline Form X of nilotinib dihydrochloride hydrate as described above, in the preparation of a medicament useful in treating or preventing a disease which respond to a protein kinase activity, including Philadelphia chromosome positive chronic myelogenous leukemia (CML) in the chronic phase.

EXAMPLES

The invention will now be further described by the following examples, which are illustrative rather than limiting.

Example 1

Preparation of Nilotinib Dihydrochloride Dihydrate 4-methyl-3-[[4-(3-pyridinyl)-2-pyrimidinyl]amino]benzoic acid (100 g, 0.326 mole) and 5-(4-methyl-1H-imidazol-1-yl)-3-(trifluoromethyl)benzenamine (78.75 g, 0.326 mole) were stirred in N-methyl pyrrolidone (700 ml) at 55-60° C. Thionyl chloride (83 ml, 0.978 mole) was added and the temperature of the reaction mass was raised to 75° C. and stirred for 6 hours. The reaction mass was cooled to 40-45° C., and water (500 ml) was added. The reaction mass was cooled to 20-25° C. and acetone (3000 ml) was added. The reaction mass was further stirred for 12 hours. The solid was isolated by filtration and washed with acetone to obtain nilotinib base.

Yield:—200 g

The wet solid was stirred in Conc. HCl (2 ml) and methanol (1000 ml) at 55-60° C. for about 1 hour and treated with carbon (2 g). The reaction mass was filtered through hyflo and the clear filtrate was distilled out completely under vacuum. The residue was stirred in mixture of water (100 ml) and methanol (100 ml). The temperature of the reaction mass was raised to 40-45° C. and stirred for 30 minutes. The reaction mass was slowly added to the acetonitrile (600 ml) at 25-30° C. and stirred for 8 hours. The reaction mass was further cooled to 0-5° C. and stirred for 1 hour. The solid was isolated by filtration, washed with acetonitrile and dried in a vacuum oven at 65-70° C. for 10 hours to obtain nilotinib dihydrochloride dihydrate.

Yield:—140 g

Example 2

Preparation of Form X Nilotinib Dihydrochloride Hydrate

Nilotinib dihydrochloride dihydrate (140 g) was dissolved in a solvent mixture of toluene (700 ml) and methanol (700 ml) at 75-80° C. After 1 hour, the reaction mass was cooled to ambient (room) temperature and further stirred for 12 hours. The solid was isolated by filtration, washed with toluene and dried in a vacuum oven at 80-85° C. for 12 hours to obtain nilotinib dihydrochloride hydrate Form X.

Yield:—122 g

Example 3

Preparation of Form X of Nilotinib Dihydrochloride Hydrate

Nilotinib dihydrochloride dihydrate (140 g) was stirred in toluene (700 ml) at 75-80° C. and methanol (700 ml) was added. After 1 hour, the reaction mass was cooled to room temperature and further stirred for 12 hours. The solid was isolated by filtration, washed with toluene and dried in a vacuum oven at 80-85° C. for 12 hours to obtain nilotinib dihydrochloride hydrate Form X.

Yield:—125 g

Example 4

Preparation of Form X of Nilotinib Dihydrochloride Hydrate

Nilotinib dihydrochloride dihydrate (100 g) was stirred in toluene (500 ml) at 25-30° C. followed by addition of methanol (500 ml). The reaction mixture was stirred and then refluxed for 1 hour. The reaction mass was then cooled to room temperature and further stirred for 12 hours. The reaction mass then cooled to 0-5° C. and maintained for 1 hour. The solid was isolated by filtration, washed with toluene (100 ml) and dried in a vacuum oven at 80-85° C. to obtain nilotinib dihydrochloride hydrate Form X.

Yield:—90 g

The invention claimed is:
1. A crystalline form of a non-stoichiometric hydrate of nilotinib dihydrochloride (Form X) characterised by:

an XRD pattern comprising peaks at 5.617, 9.941, 19.700, 20.080, 21.520, 22.620, and 24.939° and 25.60°2θ±0.2° 2θ.

2. The crystalline form according to claim 1 further characterised by an XRD pattern comprising peaks at 4.977, 12.560, 15.801, 18.180, 20.899, 27.961, 28.419, and 28.999°2θ±0.2°2θ.

3. The crystalline form according to claim 1 characterised by an XRD pattern as shown in Table 1.

4. The crystalline form according to claim 1 characterised by an XRD pattern as shown in FIG. 1.

5. The crystalline form according to claim 1 comprising from about 4.0 weight % to about 6.0 weight % of water per molecule of nilotinib.

6. The crystalline form according to claim 1 that is non-hygroscopic.

7. The crystalline form according to claim 1 that is substantially free, such that it contains less than 10% from any other crystalline and/or amorphous forms of nilotinib.

8. A process for preparing Form X according to claim 1 comprising the steps of:
    mixing nilotinib dihydrochloride dihydrate in a non-polar solvent;
    adding a polar solvent; and
    crystallizing nilotinib dihydrochloride hydrate from the resulting solution
wherein the non-polar solvent is toluene and wherein the polar solvent is methanol.

9. The process according to claim 8 wherein the volume ratio of nonpolar solvent(s) to polar solvent(s) is from about 1:1 to about 1:2.

10. The process according to claim 9 wherein the volume ratio of nonpolar solvent(s) to polar solvent(s) is about 1:1.

11. A pharmaceutical composition comprising Form X according to claim 1 and one or more pharmaceutically acceptable excipients.

12. The pharmaceutical composition according to claim 11 in the form of a tablet or capsule.

13. A method of treating Philadelphia chromosome positive chronic myelogenous leukemia (CML) comprising administering Form X according to claim 1 to a patient in need thereof.

14. The crystalline form according to claim 1 further characterised by an IR spectrum with peaks at about 3425 $cm^{-1}$, 3235 $cm^{-1}$, 3122 $cm^{-1}$, 2933 $cm^{-1}$, 2776 $cm^{-1}$, 2625 $cm^{-1}$, 1670 $cm^{-1}$, 1619 $cm^{-1}$, 1543 $cm^{-1}$, 1506 $cm^{-1}$, 1492 $cm^{-1}$ and 1114 $cm^{-1}$.

15. The crystalline form according to claim 14 characterised by an FTIR spectrum as shown in FIG. 2.

* * * * *